United States Patent [19]

Takahashi et al.

[11] Patent Number: 5,374,259
[45] Date of Patent: Dec. 20, 1994

[54] BIODEGRADABLE DISPOSABLE DIAPER

[75] Inventors: Takeshi Takahashi; Shigenori Terazono, both of Kawasaki; Takashi Fujimaki, Yokohama; Eiichiro Takiyama, Kamakura, all of Japan

[73] Assignee: Showa Highpolymer Co., Ltd., Tokyo, Japan

[21] Appl. No.: 48,190

[22] Filed: Apr. 20, 1993

[51] Int. Cl.$^5$ .................... A61F 13/15; A61F 13/20
[52] U.S. Cl. ........................... 604/367; 604/364; 604/358; 604/366; 604/370; 604/372
[58] Field of Search ............... 604/358, 372, 367, 366, 604/375, 376, 364, 370

[56] References Cited

U.S. PATENT DOCUMENTS

| | | |
|---|---|---|
| 2,999,851 | 9/1961 | Elmer . |
| 4,166,873 | 9/1979 | Gilliam . |
| 4,944,734 | 7/1990 | Wallach ............... 604/358 |
| 4,964,857 | 10/1990 | Osborn ............... 604/358 |
| 5,037,410 | 8/1991 | Zimmerman et al. . |
| 5,185,009 | 2/1993 | Sitnam ............... 604/358 |
| 5,190,533 | 3/1993 | Blackburn ............... 604/358 |
| 5,219,646 | 6/1993 | Gallagher et al. ............... 604/372 |

FOREIGN PATENT DOCUMENTS

| | | |
|---|---|---|
| 0323700 | 7/1989 | European Pat. Off. . |
| 0393819 | 10/1990 | European Pat. Off. . |
| 1059075 | 3/1954 | France . |
| 748872 | 5/1956 | United Kingdom . |
| 2243327 | 10/1991 | United Kingdom . |
| WO9110004 | 7/1991 | WIPO . |
| WO9118036 | 11/1991 | WIPO . |
| WO9300116 | 1/1993 | WIPO . |

*Primary Examiner*—Randall L. Green
*Assistant Examiner*—P. Zuttarelli
*Attorney, Agent, or Firm*—Sughrue, Mion, Zinn, Macpeak & Seas

[57] ABSTRACT

A biodegradable disposable diaper comprising a combination of a liquid absorbing material, a liquid permeable surface material and an leakproof backing material, said liquid permeable material being formed of an aliphatic polyester resin obtained by reacting an aliphatic saturated polyester prepolymer having an end group which is materially a hydroxyl group with a coupling agent or formed of said aliphatic polyester resin and an aliphatic saturated polyester resin which has not been treated by said coupling agent. The disposable diaper has excellent mechanical strength, softness, feel of touch, productivity as well as biodegradability, air permeability and waterproofness.

4 Claims, No Drawings

BIODEGRADABLE DISPOSABLE DIAPER

BACKGROUND OF THE INVENTION

1. Field of the Invention

The present invention relates to a disposable diaper in which biodegradable non-woven polyester fabric is used as a liquid permeable surface material and as an leakproof backing material. More particularly, the present invention is concerned with a disposable diaper which is not only excellent in mechanical strength, softness, waterproofness, air permeability and feel of touch but is wholly biodegradable.

2. Discussion of the Background

In recent years, disposable diaper is finding remarkably spreading use, and is facing diversified demands in regard to the quality.

Various improvements have been achieved in the constructions of disposable diapers. However, most of disposable diapers consist of a liquid permeable surface portion which contacts with the user's skin and which is generally referred to as "cover stock", a liquid absorbing portion made of fluffed pulp containing high absorbency polymer, and an leakproof backing portion for preventing water leakage generally referred to as "back sheet".

Papers were used in some old-type disposable diapers. Nowadays, however, non-woven cloths made by thermal bond method or spun-bond method are used in most disposable diapers.

On the other hand, leakproof backing material is required to excel in leakproof performance (waterproofness), softness and moisture permeability to release the internal moisture to the exterior, as well as large tear or breakage strength. It is also required not to make rustling noise.

Conventionally, the leakproof backing material has been made of a material such as a film of plasticized polymer such as polyvinyl chloride, low-density polyethylene, polypropylene, polyurethane, ethylene-vinyl acetate copolymer, ethylene-(meta)acrylic acid ester copolymer or the like, or a film which is formed by mixing a filler such as calcium carbonate in the above-mentioned film, stretched the film so as to generate micro-pores, and effecting satin-like embossing on the film.

Thus, in the known disposable diaper, the liquid permeable surface material and the leakproof backing material are not biodegradable, although the liquid absorbing material made of fluffed pulp exhibits biodegradability. Consequently, when the diaper is disposed into the ground, the surface material and the backing material remain without being degraded. For the purpose of complete disposal, therefore, it has been necessary to burn the whole diaper or to separate the liquid-permeable surface material and the leakproof backing material from the top sheet layer for separate disposal.

An object of the present invention is to develop a biodegradable disposable diaper in which a biodegradable liquid-permeable surface material and a biodegradable leakproof backing material are used in combination and which exhibits superior mechanical strength, softness, feel of touch and waterproofness, as well as high productivity. It is also an object of the present invention to develop a biodegradable disposable diaper to which air-permeability is imparted without reducing waterproofness. It is also an object of the present invention to provide a diaper having top layer of an extremely good feel of touch.

SUMMARY OF THE INVENTION

To these ends, according to the invention, there is provided a biodegradable disposable diaper comprising a combination of a liquid-absorbing material, a liquid-permeable surface material and an leakproof backing material. The liquid-permeable material and leakproof material are formed of an aliphatic polyester resin obtained by reacting an aliphatic saturated polyester prepolymer having an end group which is materially a hydroxyl group with a coupling agent. The leakproof backing material may be made of a nonwoven cloth so as to impart air-permeability to the diaper without impairing waterproofness. A nonwoven cloth may also be used as the liquid permeable surface material and/or side portions of the diaper, the nonwoven cloth being formed from an aliphatic saturated polyester treated with a coupling agent, by a dry method, spun bond method, thermal bond method, stitch bond method or needle punch method. Non-woven cloth may also be made from an aliphatic saturated polyester resin treated or not treated with a coupling agent, by melt-blown method to be used as the liquid permeable surface material or side portions of the diaper, whereby a diaper having excellent feel of touch is obtained.

The liquid absorbing material used in the present invention should have biodegradability and may be composed of a high absorbency polymer used in conventional diapers contained in, for example, fluffed pulp.

DETAILED DESCRIPTION OF THE INVENTION

The present invention will be described below in further detail.

The aliphatic polyester which is used as the liquid permeable surface material and as the leakproof backing material in the disposable diaper of the present invention mainly consists of a polyester obtained by reacting two components of glycols and dicarboxylic acid (or acid anhydrides thereof), and if necessary as a third component, with at least one polyfunctional component selected from the group consisting of trifunctional or tetrafunctional polyols, oxycarboxylic acids, and polybasic carboxylic acids (or acid anhydrides thereof). The aliphatic polyesters are prepared by reacting relatively high molecular weight polyester prepolymers which have hydroxyl groups at ends with a coupling agent so as to make them even higher molecular weight polymer.

It has been known to obtain polyurethane by reacting a low molecular weight polyester prepolymer having a number-average molecular weight of 2,000–2,500, which have hydroxyl groups as the terminal groups, with diisocyanate as a coupling agent in the preparation of rubbers, foams, coatings and adhesives.

However, the polyester prepolymers used in these polyurethane foams, coatings and adhesives are prepolymers having a low molecular weight and a number-average molecular weight of 2,000–2,500 which is the maximum that can be prepared by non-catalytic reaction. To obtain practical physical properties as the polyurethane, it is necessary that the content of diisocyanate should be as much as 10–20 parts by weight in relation to 100 parts by weight of this low molecular weight prepolymer. When such a large amount of diisocyanate is added to the low molecular weight polyester, gelation occurs so that no normal resins which can be molded in the form of a melt can be obtained.

Therefore, polyesters which are obtained by using a large amount of diisocyanate in the reaction with a low molecular weight polyester prepolymers as a raw material cannot be used as the plastic raw material for the nonwoven fabrics of the present invention.

Also, as shown in the case of polyurethane rubbers, although a method is conceivable in which hydroxyl groups are converted into isocyanate groups by the addition of diisocyanate, and then the number-average molecular weight thereof is further increased by using glycols, the same problem as mentioned above arises because 10 parts by weight of diisocyanate relative to 100 parts by weight of the prepolymer should be used in order to obtain practical physical properties. When a relatively high molecular weight polyester prepolymer is to be used, heavy metal catalysts required to prepare the prepolymer would promote the reactivity of the above-mentioned isocyanate groups to undesirably cause poor preservativity, generation of crosslinking and branching; hence a number-average molecular weight of not more than around 2,500 of polyester prepolymers would be the limit if they were to be prepared without catalysts.

The polyester prepolymers to obtain the aliphatic polyesters used in the present invention are relatively high molecular weight saturated aliphatic polyesters having substantially hydroxyl groups at the ends thereof, number-average molecular weights of at least 5,000, preferably at least 10,000, and melting point of 60° C. or higher, which are obtained by reacting glycols and dibasic carboxylic acids (or acid anhydrides thereof) in the presence of catalysts. When a prepolymer having a number-average molecular weight of lower than 5,000 is used, the small amounts of 0.1-5 parts by weight of coupling agents used in the present invention cannot provide polyesters for blow-molding having good physical properties.

When polyester prepolymers having number-average molecular weights of 5,000 or higher are used, with hydroxyl values of 30 or less, the use of small amounts of coupling agents even under severe conditions such as a molten state and the like can produce high molecular weight polyesters without gelation as the reaction is not affected by remaining catalyst.

Therefore, the polymer used in the present invention has a repeated chain structure in which a polyester prepolymer having a number-average molecular weight of 5,000 or more, preferably 10,000 or more and consisting of an aliphatic glycol and aliphatic dicarboxylic acid is combined through the urethane bonds derived from, for example, di-isocyanate as a coupling agent.

Further, the aliphatic polyester used in the present invention has a repeated chain structure in which the above-mentioned polyester prepolymer provided with branched long chains derived from polyfunctional components is combined through the urethane bonds derived from, for example, di-isocyanate as a coupling agent. When oxazoline, epoxy compounds, and acid anhydrides are used as a coupling agent, the polyester prepolymer has a repeated chain structure through ester bonds.

Hitherto, thermoplastic films or the like materials having no biodegradability were used as the liquid-permeable surface material and leakproof backing material of disposable diapers. Consequently, whole diaper was not biodegradable despite of the fact that the liquid absorption material used in the diaper is biodegradable. Consequently, these known diapers could not be wasted into the ground and could be disposed only through burning, which undesirably burdened incinerator furnaces of limited capacities.

Under this circumstance, the present invention has succeeded in obtaining a wholly biodegradable disposable diaper by using, as the materials of the liquid-permeable surface material and the leakproof backing material, an aliphatic saturated polyester resin obtained by bringing a saturated polyester prepolymer having an end group of a hydroxyl group into reaction with a coupling agent, or by using the above-mentioned aliphatic saturated polyester resin and an aliphatic saturated polyester resin which has not been treated with the coupling agent.

In addition, it is possible to remarkably improve the air-permeability without impairing the biodegradability and waterproofness, by using, as these materials, a nonwoven cloth formed by mixing or laminating webs formed from the above-mentioned polyester resin by spun-bonding or melt-blown method, thus succeeding in reducing moldering due to wear of the diaper.

The liquid-permeable surface material and the leakproof backing material produced from the above-mentioned polyester resin, when used together with the conventional liquid absorption material, provides a biodegradable disposable diaper which excels not only in the biodegradability, air permeability and waterproofness but also in mechanical strength, softness and feel of touch, and which can be produced at a high efficiency with good thermal bonding and heat set characteristics.

Examples of glycols which can be used as a reaction component include aliphatic glycols. Among them those having a straight chain alkylene group with even number carbon atoms of 2, 4, 6, 8 and 10 such as: ethylene glycol, 1,4-butanediol, 1,6-hexanediol, 1,8-octanediol, 1,10-decanediol, and mixtures thereof are preferable.

Of these glycols, those having a smaller number of carbon atoms, such as ethylene glycol, 1,4-butanediol and 1,6-hexanediol, are preferable because they can produce an aliphatic polyester having a high crystallinity and a high melting point. In particular, ethylene glycol and 1,4-butanediol are most suitable because they produce good results.

Examples of aliphatic dicarboxylic acids or anhydrides thereof which provide aliphatic polyester by reacting with glycols include aliphatic dicarboxylic acids. Among them those having a straight chain alkylene group with even number carbon atoms of 2, 4, 6, 8 and 10 such as: succinic acid, adipic acid, suberic acid, sebacic acid, 1,10-decanedicarboxylic acid, succinic anhydride and mixtures thereof are preferable. Of these dicarboxylic acids, those having a smaller number of carbon atoms, such as succinic acid, adipic acid and succinic anhydride, are preferable because they can produce an aliphatic polyester having high crystallinity and high melting points. In particular, succinic acid, succinic anhydride and an acid mixture of succinic acid or succinic anhydride and another dicarboxylic acid such as adipic acid, suberic acid, sebacic acid or 1,10-decandicarboxylic acid are preferable.

In the system of an acid mixture containing two or more acid components, for example, succinic acid and other dicarboxylic acids, the mixing ratio of succinic acid is at least 70 mol %, preferably at least 90 mol %, and the mixing ratio of the other carboxylic acids is 30 mol % or less, preferably 10 mol % or less.

A combination of 1,4-butanediol and succinic acid or succinic anhydride and a combination of ethylene glycol and succinic acid or succinic anhydride are particularly preferable for the present invention because the combinations exhibit melting points close to that of polyethylene.

(Third Component)

To these glycols and dicarboxylic acid, if necessary, may be added as a third component at least one polyfunctional component selected from the group consisting of trifunctional or tetrafunctional polyols, oxycarboxylic acid, and polybasic carboxylic acids (or acid anhydrides thereof). The addition of this third component, which causes the branching of long chains, can impart desirable properties in molten state to the polyester prepolymer, because the ratio of weight-average molecular weight (MW)/number-average molecular weight (Mn), i.e., the molecular weight distribution, increases with increases in its molecular weight.

In terms of the amount of polyfunctional components to be added without fear of gelation, a trifunctional component of 0.1–5 mole %, or a tetrafunctional component of 0.1–3 mole % is added relative to 100 mole % of the total of aliphatic dicarboxylic acid (or acid anhydride thereof) components.

(Polyfunctional Components)

Examples of polyfunctional components as the third component include trifunctional or tetrafunctional polyols, oxycarboxylic acids, and polybasic-carboxylic acids.

The trifunctional polyols alcohols representatively include trimethylol propane, glycerin or anhydrides thereof. The tetrafunctional polyols representatively include pentaerythritol.

The trifunctional oxycarboxylic acid components are divided into the two types of (i) a component which has two carboxyl groups and one hydroxyl group in one molecule, and (ii) another component which has one carboxyl group and two hydroxyl groups in one molecule. Malic acid which has two carboxyl groups and one hydroxyl group in one molecule becomes practical and sufficient to the purposes of the present invention in view of commercial availability at low cost.

The tetrafunctional oxycarboxylic acid components are the following three types of components:

(i) A component which has three carboxyl groups and one hydroxyl group in one molecule;
(ii) Another component which has two carboxyl groups and two hydroxyl group in one molecule; and
(iii) The remaining component which has three hydroxyl groups and one carboxyl group in one molecule. Any type can be used, though in view of commercial availability at low cost, citric acid and tartaric acid are practical and sufficient to the purposes of the present invention.

As a trifunctional polybasic carboxylic acid (or acid anhydride thereof) component trimesic acid, propane tricarboxylic acid and the like can be used. Among them, trimesic anhydride is practical for the purposes of the present invention.

As a tetrafunctional polybasic-carboxylic acid (or anhydride thereof) various types of aliphatic compounds, cycloaliphatic compounds, aromatic compounds and the like, described in certain literatures, can be used. In view of commercial availability, for example, pyromellitic anhydride, benzophenone tetracarboxylic anhydride and cyclopentane tetracarboxylic anhydride are practical and sufficient to the purposes of the present invention.

These glycols and dibasic acids are mainly consisted of aliphatic series, while small amounts of other components, for example, aromatic series may be concomitantly used. These other components may be blended or copolymerized in amounts up to 20% by weight, preferably up to 10% by weight, and more preferably up to 5% by weight because using these compounds degrades biodegradability.

The polyester prepolymer for aliphatic polyesters to be used in the present invention has hydroxyl groups at the terminals. To introduce the hydroxyl groups, it is necessary that glycols are used somewhat excessively.

For preparation of the polyester prepolymer having a relatively high molecular weight, it is necessary to use deglycol-reaction catalysts in the deglycol reaction subsequent to the esterification.

Examples of the deglycol-reaction catalysts include titanium compounds such as acetoacetoyl type titanium chelate compounds and organic alkoxy titanium compounds and the like. These titanium compounds can be used in combination. Examples of compounds used in combination include diacetoacetoxy oxytitanium (Nippon Chemical Industry Co., Ltd.; Nursem Titanium) tetraethoxy titanium, tetrapropoxy titanium, tetrabutoxy titanium and the like. The amount of the titanium compound used is 0.001–1 part by weight, and preferably 0.01–0.1 part by weight relative to 100 parts by weight of the polyester prepolymer. These titanium compounds may be blended before the esterification, or may be blended immediately before the deglycol-reaction.

As a result, polyester prepolymers having an number-average molecular weight of at least 5,000, and preferably at least 20,000 and a melting point of 60° C. or higher, can be generally obtained easily. It is even more preferable if these polyester prepolymers have crystallinity.

To the polyester prepolymer which has a number-average molecular weight of at least 5,000, preferably at least 10,000, and whose terminal groups are substantially hydroxyl groups may be added coupling agents in order to increase its number-average molecular weight.

When an aliphatic polyester not treated with coupling agent is used, it is not essential that the end group is a hydroxyl group but it is specifically required that esterification is conducted sufficiently. Thus, a flow characteristic of at least 300 to 1000 g/10 min or so in terms of MFR (190° C.) is required.

The coupling treatment is to bring the above-mentioned polyester prepolymer into reaction with a coupling agent so as to form aliphatic saturated polyester resin. Diisocyanate, exazoline, diepoxy compound or acid anhydride can be used as the coupling agent. It is, however, preferred to use diisocyanate, in view of reactivity and performance of polyester produced with this coupling agent.

Although not limited, examples of diisocyanate include 2,4-tolylene diisocyanate, a mixture of 2,4-tolylene diisocyanate and 2,6-tolylene diisocyanate, diphenylmethane diisocyanate, 1,5-naphthylene diisocyanate, xylylene diisocyanate, hydrogenated xylylene diisocyanate, hexamethylene diisocyanate, isophorone diisocyanate and the like. Particularly, hexamethylene diisocyanate is preferably used in terms of hue of prepared resins, reactivity at the time of blending polyesters, and the like.

When oxazoline or diepoxy compound is used as the coupling agent, introduction of the coupling agent should be conducted after bringing the hydroxyl group of the prepolymer into reaction with the acid anhydride so as to change the end of the hydroxyl group into carboxyl group.

The amount of the coupling agent to be used varies depending on whether a film or a non-woven cloth is used and, when non-woven cloth is used, whether the nonwoven cloth is formed by spun-bond method or melt-blown method. In general, however, the content of the coupling agent ranges from 0.1 to 5 weight parts, preferably from 0.5 to 3 weight parts, for 100 weight parts of the polyester prepolymer.

The coupling reaction does not take place sufficiently when the content of the coupling agent is 0.1 weight parts or below. On the other hand, gelation becomes noticeable when the same exceeds 5 weight parts.

The addition is preferably performed when the polyester is in a uniformly melted state under easily stirrable conditions. Although it is not impossible for the coupling agents to be added to the polyester prepolymer in the form of a solid and melted and mixed through an extruder, adding the agents in a polyester preparation unit, or adding them to polyester prepolymer in a molten state (for example, in a kneader) is more practical.

A coupling-treated highly fluid resin is preferably used when melt-blown method is adopted. The treatment with coupling agent, however, may be omitted when a resin having a specifically low melt viscosity is used.

It is needless to say that when the above-mentioned aliphatic polyester is used to obtain the disposable diaper according to the present invention, if necessary, lubricants, waxes, coloring agents and crystallizing promoters as well as antioxidants, thermal stabilizers, UV absorbers and the like can be used concomitantly.

That is, antioxidants include hindered phenol antioxidants such as p-tert-butyl hydroxytoluene and p-tertbutyl hydroxyanisole, sulfur antioxidants such as distearyl thiodipropionate and dilauryl thiodipropionate, and the like; heat stabilizers include triphenyl phosphite, trilauryl phosphite, tris-nonylphenyl phosphite and the like; UV absorbers include p-tert-butyl phenyl salicylate, 2-hydroxy-4-methoxybenzophenone, 2-hydroxy-4-methoxy-2'-carboxybenzophenone, 2,4,5-trihydroxybutylophenone and the like; lubricants include calcium stearate, zinc stearate, barium stearate, sodium palmirate and the like; antistatic agents include N,N-bis(hydroxyethyl) alkyl amine, alkyl amine, alkyl allyl sulfonate, alkyl sulfonate and the like; flame retarders include hexabromocyclododecane, tris-(2,3-dichloropropyl) phosphate, pentabromophenyl allyl ether and the like; inorganic fillers include calcium carbonate, silica, titanium oxide, talc, mica, barium sulfate, alumina and the like; crystallizing promoters include polyethylene terephthalate, poly-trans-cyclohexane dimethanol terephthalate and the like.

The biodegradable polyester resin obtained through the above-described process is formed into a non-woven cloth and such a cloth is used as the liquid-permeable surface material in the present invention. The leakproof backing material may be a film or a non-woven cloth of the biodegradable polyester.

When the biodegradable polyester is used in the form of a film, the film can be formed by inflation method or T-die method as in the case of conventional thermoplastic resins. In such a case, the film may be formed by mixing a filler such as calcium carbonate, extruding the film material into the form of a film, stretching the film and effecting a staining emboss work, thereby obtaining leakproof backing material having high air permeability, as in the cases of other types of resins. The film thickness preferably ranges, as in the case of the cloth, from 20 to 50 $\mu$m, so that the biodegradable backing material in the form of film can have mechanical strength, softness, waterproofness and air-permeability equivalent to those of the nonwoven material.

The air-permeability of the film having micro-pores formed by stretching from the material containing filler is still insufficient, and "moldering" inevitably occurs more or less. In view of this fact, the present invention also aims at developing an leakproof backing material having improved air-permeability without reduction in the waterproofness as well as the biodegradability.

It was found that an leakproof air-permeable biodegradable disposable diaper is obtained when the leakproof backing material is a non-woven cloth formed by laminating webs prepared from the above-mentioned polyester resin by spun-bond method (generally, fibers of 0.3 to 10 d are obtained) or by melt-blown method (generally, fibers of 0.01 to 1 d are obtained).

The melting characteristic of the polyester resin used in the present invention is easily controllable by selecting the molecular weight of the polyester prepolymer or the content of the coupling agent. In addition, since the fibers obtained can easily be bonded by thermal bonding, the non-woven cloth tan be produced with an extremely high yield by spun-bond method, melt-blown method, step-bond method and needle punch method.

Preferably, the leakproof backing material is formed by superposing 95 to 50 weight % of web formed by spun bond method and 5 to 50 weight % of web formed by melt-blown method, or mixing fibers formed by these methods on a line so as to form a non-woven cloth. The use of non-woven cloth from the spun-bond fibers alone is not preferred because such a non-woven cloth exhibits inferior waterproofness although the air-permeability is high, whereas the use of non-woven cloth formed from melt-blown fibers alone exhibits inferior strength although it exhibits superior waterproofness, so that this type of non-woven cloth has to have a large thickness to provide the required level of strength.

When the non-woven cloth is formed by mixing spun-bond and melt-blown fibers or laminating web of these fibers, it is preferred that the portion constituted by the melt-blown fibers which are thinner is placed on the inner side which is contactable with the user's body.

The leakproof backing material preferably has a waterproof pressure of 1000 mmH$_2$O or greater, moisture permeability of 2500 to 6000 g/m$^2$.24 hr, and air-permeability of 200 to 1000 sec/100 cc or so. Such characteristics can easily be realized by using a non-woven cloth formed from the fiber mixture in which spun-bond fibers and melt-blown fibers are mixed. Owing to the use of the non-woven fiber, it is possible to obtain a high waterproof pressure equivalent to that of films which are materially water-impermeable at the pressure of 2000 mmH$_2$O or higher, while maintaining the moisture permeability and air-permeability at high levels of 2500 to 6000 g/m$^2$ and 700 to 900 sec/100 cc. It is therefore possible to greatly reduce moldering and, hence, to prevent eruption on the skin due to wear of the diaper.

On the other hand, when a web or non-woven cloth produced from the above-mentioned polyester resin is used as the material of the liquid-permeable surface material, the web or non-woven cloth is formed from comparatively thick fibers such as those formed by thermal bonding (core sheath method) or spun-bond method from the polyester resin specified by the present invention.

Such a web or non-woven cloth exhibits high air-permeability and small water absorption unlike pulp-type tissue or cotton, thus offering improved feel of touch.

A high level of water-repelling nature is required particularly at the side portions of the liquid-permeable surface material. Preferably, a non-woven cloth formed from the polyester resin by melt-blown method and spun-bond method is used as the material for such side portions. The use of non-woven cloth formed by the melt-blown method alone cannot provide sufficiently high strength, whereas the use of the non-woven cloth formed by spun-bonding cannot provide sufficient water-repelling effect due to too larger fiber thickness, although a satisfactorily high level of strength is obtained. It is possible to form both the liquid-permeable surface material and the leakproof backing material from the same polyester resin. In such a case, a high yield of disposable diaper is obtained advantageously, because the thermal bonding can be conducted very easily.

Needless to say, from the view point of biodegradation, it is preferred that portions of the disposable diaper other than fluffed pulp or elastics, e.g., waist band, is made from the above-mentioned polyester resin.

According to the present invention, the disposable diaper employs a liquid-permeable surface material made of a biodegradable polyester resin, in combination with an leakproof backing material which is biodegradable. Consequently, the whole diaper is biodegradable, thus overcoming the problem of destruction of environment which otherwise would be caused when these diapers are disposed into the ground.

In addition, the leakproof backing material made of a non-woven cloth provides sufficient air-permeability without impairing waterproofness, thus reducing moldering in the diaper.

Furthermore, the diaper can be produced with improved production efficiency by thermal bonding, when the liquid-permeable surface material is formed of a web or non-woven cloth by thermal bonding (core sheath method) or spun-bonding from the above-mentioned biodegradable polyester resin.

EXAMPLES

Methods of the present invention are illustrated with reference to the following examples, but the invention is not intended to be limited only thereto.

(The Method of the Synthesis of the Resin)
(Resin B1)

A 700 L reactor was purged with nitrogen, then 183 kg of 1,4-butanediol and 224 kg of succinic acid were charged in it. After the temperature was elevated under nitrogen stream, esterification by dehydration condensation was carried out for 3.5 hr at 192°–220° C., and after ceasing nitrogen charge, for further 3.5 hr under reduced pressures of 20-2 mmHg. A sample collected had an acid value of 9.2 mg/g, a number-average molecular weight (Mn) of 5,160 and a weight average molecular weight (Mw) of 10,670. Subsequently, 34 g of tetraisopropoxy titanium, a catalyst, was added at normal pressures under nitrogen stream. The temperature was elevated to carry out a deglycol-reaction at temperatures of 215°–220° C. under reduced pressures of 15-0.2 mmHg for 5.5 hr. A sample collected had a number-average molecular weight (Mn) of 16,800 and a weight average molecular weight (Mw) of 43,600. The yield of resulting polyester prepolymer (A1) was 339 kg except condensate water.

5.42 kg of hexamethylene diisocyanate was added to the reactor containing 339 kg of the polyester prepolymer (A1) to perform a coupling reaction for 1 hr at 180°–200° C. The viscosity was rapidly increased, but no gelation occurred. Then, 1.70 kg of Irganox 1010 (Ciba-geigy) as an antioxidant and 1.70 kg of calcium stearate as a lubricant were added, and the mixture was further stirred for 30 min. The resulting reaction product was extruded into water, and cut by a cutter into pellets. The aliphatic polyester (B1) obtained after drying in a vacuum at 90° C. for 6 hr had a yield of 300 kg.

The obtained polyester (B1) was a slightly ivorylike white, waxy crystal, and had a melting point of 110° C., a number-average molecular weight (Mn) of 35,500 a weight-average molecular weight (Mw) of 170,000, a MFR (190° C.) of 1.0 g/10 min, a viscosity of 230 poises in a 10% ortho-chlorophenol solution and a melt viscosity of $1.5 \times 10^4$ poises at a temperature of 190° C. at a shear rate of 100 sec$^{-1}$. The average-molecular weight was measured by a Shodex GPC System-11 (Showa Denko, gel permiation chromatography) using a HFIPA solution containing 5 mmol $CF_3COONa$ (concentration of 0.1% by weight) as a medium. A calibration curve was drawn using a PMMA standard sample (Shodex Standard M-75, Showa Denko).

(Resin B2)

A 700 L reactor was purged with nitrogen, then 200 kg of 1,4-butanediol, 250 kg of succinic acid and 2.84 kg of trimethylol propane were charged in it. After the temperature was elevated under nitrogen stream, esterification by dehydration condensation was performed for 3.5 hr at 192°–220° C., and after ceasing nitrogen charge, for further 3.5 hr under reduced pressures of 20-2 mmHg. A sample collected had an acid value of 2.5 mg/g, a number-average molecular weight (Mn) of 8,660 and a weight-average molecular weight (Mw) of 9,520. Subsequently, 37 g of tetraisopropoxy titanium, a catalyst, was added at normal pressures under nitrogen stream. The temperature was elevated to perform a deglycol-reaction at temperatures of 215°–220° C. under reduced pressures of 15-0.3 mmHg for 8.0 hr. A sample collected had a number-average molecular weight (Mn) of 16,200 and a weight-average molecular weight (Mw) of 67,900. The resulting polyester (A2) had a yield of 367 kg except condensate water of 76 kg.

330 g of hexamethylene diisocyanate was added to the reactor containing 367 kg of polyester (A2) to perform a coupling reaction for 1 hr at 170°–185° C. The viscosity was rapidly increased, but no gelation occurred. Then, 370 g of Irganox 1010 (Ciba-geigy) as an antioxidant and 370 g of calcium stearate as a lubricant were added, and the mixture was further stirred for 30 min. The resulting reaction product was extruded into water by an extruder, and cut by a cutter into pellets. The polyester (B2) obtained after drying in a vacuum at 90° C. for 6 hr had a yield of 360 kg.

The obtained polyester (B2) was a slightly ivorylike white, waxy crystal, and had a melting point of 110° C., a number-average molecular weight (Mn) of 25,600 a weight-average molecular weight (Mw) of 120,000, a MFR (190° C.) of 18 g/10 min and a melt viscosity of $4.0 \times 10^4$ poises at a temperature of 190° C. at a shear rate of 100 sec$^{-1}$. The average molecular weight was measured as described above.

(Resin B3)

A 700 L reactor was purged with nitrogen, then 196 kg of 1,4-butanediol and 204 kg of succinic acid were charged in it. After the temperature was elevated under nitrogen stream, esterification by dehydration condensation was carried out for 5.0 hr at 192°–220° C., and after ceasing nitrogen charge, for further 3.5 hr under reduced pressures of 15-2 mmHg. A sample collected had an acid value of 8.5 mg/g, a number-average molecular weight (Mn) of 5,200 and a weight average molecular weight (Mw) of 10,100. Subsequently, 30 g of tetraisopropoxy titanium, a catalyst, was added at normal pressures under nitrogen stream. The temperature was elevated to carry out a deglycol-reaction at temperatures of 215°–220° C. under reduced pressures of 5-0.2 mmHg for 15 hr. A sample collected had a number-average molecular weight (Mn) of 23,300 and a weight average molecular weight (Mw) of 89,300 (Mw/Mn=5.4). The yield of resulting polyester prepolymer (A3) was 327 kg except condensate water.

41 g of phosphorous acid as an anti-coloring agent, 327 g of Irganox B225 (Ciba-geigy) as an antioxidant and 327 g of calcium stearate as a lubricant were added to the reactor containing 327 kg of the polyester prepolymer (A3) cooled to 180° C., and the mixture was further stirred for 30 min. The resulting reaction product was extruded into water, and cut by a cutter into pellets. The aliphatic polyester (B3) obtained after drying in a vacuum at 90° C. for 6 hr had a yield of 310 kg.

The obtained polyester (B3) was a white, solid crystal, and had a melting point of 120° C., a number-average molecular weight (Mn) of 23,100 a weight-average molecular weight (Mw) of 90,500, a MFR (190° C.) of 500 g/10 min, a viscosity of 20 poises in a 10% orthochlorophenol solution and a melt viscosity of 100 poises at a temperature of 190° C. at a shear rate of 1–10 sec$^{-1}$ (Tochimeck, rotary ciscometer). The average molecular weight was measured as described above.

(Resin B4)

A 700 L reactor was purged with nitrogen, then 222.5 kg of 1,4-butanediol and 277.5 kg of succinic acid were charged in it. After the temperature was elevated under nitrogen stream, esterification by dehydration condensation was carried out for 5.0 hr at 195°–210° C., and after ceasing nitrogen charge, for further 3.5 hr under reduced pressures of 15-5 mmHg. A sample collected had an acid value of 9.1 mg/g, a number-average molecular weight (Mn) of 5,300 and a weight average molecular weight (Mw) of 11,200. Subsequently, 30 g of tetraisopropoxy titanium, a catalyst, was added at normal pressures under nitrogen stream. The temperature was elevated to carry out a deglycol-reaction at temperatures of 215°–220° C. under reduced pressures of 5-0.2 mmHg for 7.5 hr. A sample collected had a number-average molecular weight (Mn) of 17,200 and a weight average molecular weight (Mw) of 58,700. The yield of resulting polyester prepolymer (A4) was 415.5 kg except condensate water.

52 g of phosphorous acid as an anti-coloring agent, 416 g of Irganox 1010 (Ciba-geigy) as an antioxidant and 416 g of calcium stearate as a lubricant were added to the reactor containing 415.5 kg of the polyester prepolymer (A4), and the mixture was further stirred for 30 min. The resulting reaction product was extruded into water, and cut by a cutter into pellets. The aliphatic polyester (B4) obtained after drying in a vacuum at 90° C. for 6 hr had a yield of 410 kg.

The obtained polyester (B4) was a white, solid crystal, and had a melting point of 120° C., a number-average molecular weight (Mn) of 26,700 a weight-average molecular weight (Mw) of 98,000, a MFR (190° C.) of 120 g/10 min and a melt viscosity of 700 poises at a temperature of 190° C. at a shear rate of 1–10 sec$^{-1}$ (Tochimeck, rotary viscometer).

Pellets of these resins were dried for 2 to 4 hours at 100° to 120° C. in a hot-air circulation drier of dew-point adjusting type, and were then subjected to forming.

[Inflation Film]

Calcium carbonate was mixed into the resin (B1), and the mixture was extruded by a 60 mm$\phi$ extruder employing a circular die having a lip gap of 1.2 mm and a diameter of 300 mm, at a blow-up ratio of 3.0 and a take-up speed of 135 m/min, whereby an inflation film of 30$\mu$m thick was obtained. The film was then treated to become a satinized film. The film exhibited a strength of 650 kg/cm$^2$ in the MD direction and 670 kg/cm$^2$ in the TD direction. The elongation was 660% in the MD direction and 790% in the TD direction.

[Spun-Bond/Melt-Blown Non-Woven Fabric]

A specific apparatus was employed which could form non-woven fabrics of spun-bond fibers and melt-blown fibers by an in-line type production process.

The spun-bonding was conducted by extruding the resin (B2) from an extruder of 65 mm$\phi$. having a 200-hole, 5 rows die having a dies width of 1000 mm. On the other hand, the melt-blown method was carried out by extruding the resin C from an extruder of 40 mm$\phi$, having 1000 holes by 1 mm pitch, 1-row die using superheated steam of 2.5 kg/cm$^2$ G as the high-velocity injection gas.

Filaments spun by spun bond method were deposited on a collect conveyor and were thermally bonded together by the action of a pair of thermal bonding devices having flat rolls and engraved rolls, whereby spun-bond non-woven fabric was obtained.

The spun-bond/melt-blown process was carried out by jetting melt-blown filaments onto the spun-bond filament web which is being conveyed by the collect conveyor, and spinning, mixing and depositing these fibers with the web, followed by press bonding performed by the same thermal bonding devices, whereby an SB-MB mixture non-woven cloth was obtained.

[Thermal-Bond Non-Woven Fabric]

The resin B2 was continuously extruded through an extruder of 40 mm diameter having a multi-filament nozzle with 68 holes of 0.6 mm$\phi$, followed by stretching, crimping and cutting at a length of 52 mm, whereby staple fibers were obtained. The monofilament of this fiber showed a size of 4.3 denier, strength of 42 g/d and elongation of 43%.

The fibers were cut by a cutting machine and deposited so as to be formed into a web which was then press-bonded by a calender roll, whereby a thermal-bond non-woven fabric was obtained.

[Production of Diaper]

A polymer having high water absorbency was placed in fluffed pulp and wrapped by an absorbing paper, whereby a liquid absorption portion was formed. Front and rear films or non-woven fabrics were bonded together with the liquid absorption portion sandwiched therebetween, whereby a diaper was obtained.

(EXAMPLE 1)

A spun-bond non-woven cloth of the resin (B1), having a weight of 20 g/m² and a thickness of 0.19 mm was used as the liquid-permeable surface material. Fluffed pulps containing polymer having high water absorbency were used as the liquid absorption material. An inflation film of 30 mm thick of the resin (B1) was used as the leakproof backing material. A biodegradable disposable diaper was formed by using these materials. The performances of the materials used are shown in Table 1.

The diaper was impregnated with 200 cc of artificial urine and was buried under the ground. The diaper was wholly degraded and decomposed almost completely in 3 months.

(EXAMPLE 2)

A thermal-bond non-woven cloth of the resin B2, having a weight of 20 g/m² and a thickness of 0.19 mm was used as the liquid-permeable surface material. The liquid absorption material and the leakproof backing material were made of the same materials as those used in Example 1. The performances of the materials used are shown in Table 1.

The diaper was buried under the ground in the same manner as in Example 1. The diaper was wholly decomposed almost completely in 3 months.

(EXAMPLE 3)

A melt-blown web of the resin (B3) having a weight of 15 g/cm² was superposed on a thermal-bond web of resin (B3) having a weight of 45 g/m². Both webs were press-bonded by means of emboss rolls, whereby a nonwoven fabric having a weight of 60 g/m² and a thickness of 0.5 mm was obtained. A disposable diaper was produced under the same conditions as those in Example 2 except that this nonwoven fabric was used as the leakproof backing material. Performances of the materials used are shown in Table 1.

This diaper was subjected to the same biodegradation test as that of Example 1. The diaper was eroded and degraded almost completely in 3 months.

(EXAMPLE 4)

A melt-blown web of the resin (B4) having a weight of 15 g/cm² was deposited on and mixed with a spun-bond web of resin (B2) having a weight of 45 g/m². Both webs were press-bonded, whereby a nonwoven fabric having a weight of 60 g/m² was obtained. A disposable diaper was produced under the same conditions as those in Example 1 except that this nonwoven cloth was used as the anti-leakage backing material. Performances of the materials used are shown in Table 1.

This diaper was subjected to the same biodegradation test as that of Example 1. The diaper was eroded and degraded almost completely in 3 months.

(EXAMPLE 5)

A melt-blown web of the resin (B3) having a weight of 2 g/cm² was deposited on and mixed with a spun-bond web of resin (B2) having a weight of 18 g/m². Both webs were press-bonded, whereby a nonwoven cloth having a weight of 20 g/m² was obtained. A disposable diaper was produced under the same conditions as those in Example 1 except that this non-woven cloth was used as the leakproof backing material. Performances of the materials used are shown in Table 1.

This diaper was subjected to the same biodegradation test as that of Example 1. The diaper was eroded and degraded almost completely in 3 months.

TABLE 1

| | Examples | | | | | | | | | |
|---|---|---|---|---|---|---|---|---|---|---|
| | 1 | | 2 | | 3 | | 4 | | 5 | |
| Positions | Obvers | Revers | Obvers | Revers | Obvers | Revers | Obvers | Revers | Obvers | Revers |
| Construction | SB | Film | TB | Film | TB | TB/MB | SB | SB/MB | SB/MB | Film |
| Weight (g/m²) | 20 | 30 | 20 | 30 | 20 | 45/15 | 20 | 45/15 | 18/2 | 30 |
| Thickness (mm) | 0.19 | 0.03 | 0.22 | 0.03 | 0.22 | 0.50 | 0.19 | 0.45 | 0.2 | 30 |
| Strength | | | | | | | | | | |
| MD | 70 | 650 | 80 | 650 | 80 | 150 | 70 | 170 | 120 | 650 |
| TD | 60 | 670 | 65 | 670 | 65 | 140 | 60 | 165 | 155 | 670 |
| Elongation | | | | | | | | | | |
| MD (%) | 25 | 660 | 40 | 660 | 40 | 45 | 25 | 29 | 24 | 660 |
| TD (%) | 26 | 790 | 35 | 790 | 35 | 40 | 26 | 28 | 35 | 790 |
| Water proof pressure (mm) | | 2100 | | 2100 | | 700 | | 600 | | 2100 |
| Moisture permeability (g/m² · 24 hr) | | 4300 | | 4300 | | 5500 | | 5500 | | 4300 |
| Air permeability (sec/100 cc) | | 900 | | 900 | | 350 | | 400 | | 900 |

Strength is expressed in terms of g/50 mm width/g in case of non-woven cloth and in terms of kg/cm² in case of film.

What is claimed is:

1. A biodegradable disposable diaper comprising, in order, a liquid permeable surface material, a liquid absorbing material, and a leakproof backing material,
   wherein said liquid permeable surface material is attached to said liquid absorbing material, and said liquid absorbing material is attached to said leakproof backing material,
   wherein said liquid permeable surface material and said leakproof backing material are
   (1) formed of an aliphatic polyester resin obtained by reacting an aliphatic saturated polyester prepolymer having an end group which is a hydroxyl group with a coupling agent or
   (2) formed of
     (A) an aliphatic polyester resin obtained by reacting an aliphatic saturated polyester prepolymer having an end group which is a hydroxyl group with a coupling agent and
     (B) an aliphatic saturated polyester resin which has not been treated by said coupling agent, wherein the leakproof backing material is made from less coupling agent than the liquid permeable surface material.

2. A biodegradable disposable diaper as claimed in claim 1, wherein the leakproof backing material made of aliphatic polyester resin is a non-woven fabric.

3. A biodegradable disposable diaper as claimed in claim 2, wherein the leakproof backing material made of aliphatic polyester resin is a non-woven fabric formed by mixing fibers or laminating webs formed by a spun-bond method and melt-blown method.

4. A biodegradable disposable diaper as claimed in any one of claims 1 to 3, wherein a non-woven fabric is used as said liquid permeable surface material, said non-woven fabric being formed (1) from non-woven fabric formed by a dry method, spun bond method, thermal bond method, stitch bond method or needle punch method using an aliphatic saturated polyester treated with a coupling agent or (2) from
  (A) non-woven fabric formed by a dry method, spun bond method, thermal bond method, stitch bond method, or needle punch method using an aliphatic saturated polyester treated with a coupling agent and
  (B) filaments or non-woven fabric formed by a melt-blown method using an aliphatic saturated polyester resin, which has been treated with a coupling agent or which has not been treated with a coupling agent.

* * * * *